United States Patent
Daniel et al.

(10) Patent No.: US 9,725,827 B2
(45) Date of Patent: Aug. 8, 2017

(54) PROCESS FOR PRODUCING WATER-ABSORBING POLYMER FIBERS

(71) Applicant: BASF SE, Ludwigshafen (DE)

(72) Inventors: Thomas Daniel, Waldsee (DE); Xiaomin Zhang, Charlotte, NC (US); Kathleen H. Goebel, Charlotte, NC (US)

(73) Assignee: BASF SE, Ludwigshafen (DE)

( * ) Notice: Subject to any disclaimer, the term of this patent is extended or adjusted under 35 U.S.C. 154(b) by 107 days.

(21) Appl. No.: 14/430,932

(22) PCT Filed: Sep. 23, 2013

(86) PCT No.: PCT/EP2013/069666
§ 371 (c)(1),
(2) Date: Mar. 25, 2015

(87) PCT Pub. No.: WO2014/053345
PCT Pub. Date: Apr. 10, 2014

(65) Prior Publication Data
US 2015/0292117 A1    Oct. 15, 2015

Related U.S. Application Data

(60) Provisional application No. 61/708,656, filed on Oct. 2, 2012.

(51) Int. Cl.
| | |
|---|---|
| *A61F 13/53* | (2006.01) |
| *A61L 15/24* | (2006.01) |
| *D01F 6/16* | (2006.01) |
| *D06M 10/00* | (2006.01) |
| *D01D 5/00* | (2006.01) |
| *D01D 10/00* | (2006.01) |
| *D01F 6/02* | (2006.01) |
| *A61L 15/60* | (2006.01) |
| *D01F 6/26* | (2006.01) |
| *D06M 101/18* | (2006.01) |
| *D06M 101/26* | (2006.01) |

(52) U.S. Cl.
CPC ............... *D01F 6/16* (2013.01); *A61L 15/24* (2013.01); *A61L 15/60* (2013.01); *D01D 5/003* (2013.01); *D01D 5/0007* (2013.01); *D01D 10/00* (2013.01); *D01F 6/02* (2013.01); *D01F 6/26* (2013.01); *D06M 10/001* (2013.01); *A61F 2013/53062* (2013.01); *A61F 2013/530613* (2013.01); *D06M 2101/18* (2013.01); *D06M 2101/26* (2013.01); *D10B 2321/08* (2013.01); *D10B 2509/00* (2013.01); *D10B 2509/02* (2013.01)

(58) Field of Classification Search
CPC .......... A61F 2013/530613; A61F 2013/53062; A61L 15/24; D01D 20/00; D01F 6/16; D06M 10/001
See application file for complete search history.

(56) References Cited

U.S. PATENT DOCUMENTS

| | | |
|---|---|---|
| 3,867,499 A | 2/1975 | Morgan |
| 4,913,869 A | 4/1990 | Funk |
| 4,962,172 A | 10/1990 | Allen et al. |
| 5,147,956 A | 9/1992 | Allen |
| 5,614,296 A | 3/1997 | Travelute et al. |
| 5,667,743 A | 9/1997 | Tai et al. |
| 5,756,159 A | 5/1998 | Hoskins et al. |
| 5,980,996 A | 11/1999 | Terry et al. |
| 6,342,298 B1 | 1/2002 | Evans et al. |
| 2006/0057375 A1* | 3/2006 | Harren ............ D01D 5/00 428/364 |
| 2013/0146810 A1* | 6/2013 | Zhang ............ B01J 20/28023 252/194 |
| 2014/0039150 A1* | 2/2014 | Ellison ............ C08F 2/46 528/294 |

FOREIGN PATENT DOCUMENTS

| | | |
|---|---|---|
| CN | 101021017 A | 8/2007 |
| EP | 0 268 498 A2 | 5/1988 |
| GB | 2327201 A | 1/1999 |
| JP | H1018125 A | 1/1998 |
| JP | 2003073919 A | 3/2003 |
| WO | WO-98/24832 A1 | 6/1998 |
| WO | WO-2008/049397 A2 | 5/2008 |
| WO | WO-2013/083698 A1 | 6/2013 |

OTHER PUBLICATIONS

Gupta, P., et al., "In situ Photo-Cross-Linking of Cinnamate Functionalized Poly (methyl methacrylate-co-2-hydroxyethyl acrylate) Fibers During Electrospinning." *Macromolecules* (2004), vol. 37, No. 24, pp. 9211-9218.

Reneker, D. H., et al., "Nanometre Diameter Fibres of Polymer, Produced by Electrospinning." *Nanotechnology* (1996), vol. 7, No. 3, pp. 216-223.

International Search Report in International Application No. PCT/EP2013/069666, dated Dec. 16, 2013.

* cited by examiner

*Primary Examiner* — Lynne Anderson

(74) *Attorney, Agent, or Firm* — Marshall, Gerstein & Borun LLP

(57) ABSTRACT

The invention relates to a process for producing water-absorbing crosslinked polymer fibers, especially micro- or nanofibers, by spinning process, especially electrospinning process and to fibers obtainable by this process.

17 Claims, No Drawings

PROCESS FOR PRODUCING WATER-ABSORBING POLYMER FIBERS

CROSS-REFERENCE TO RELATED APPLICATIONS

This application is the U.S. National Phase of PCT Application No. PCT/EP2013/069666, filed Sep. 23, 2013, which claims the benefit U.S. Provisional patent application No. 61/708,656, filed Oct. 2, 2012, incorporated herein by reference in its entirety.

The present invention relates to a process for producing water-absorbing crosslinked polymer fibers, especially micro-or nanofibers, by electrospinning process and to fibers obtainable by this process.

Water-absorbing polymer particles ("super absorbent polymer", SAP) are widely used in sanitary goods and hygiene articles such as disposable diapers, adult incontinence pads and catamenial products as sanitary napkins. Water absorbing resins are available in a variety of chemical forms.

The production of SAP particles is described in the monograph "Modern Superabsorbent Polymer Technology", F. L. Buchholz and A. T. Graham, Wiley-VCH, 1998, pages 71 to 103.

Much effort is taken to very thin absorbent articles such as diapers or sanitary napkins, because they fit better and less noticeable and as article packaging is more compact they easier to carry and to store and therefore the distribution costs are reduced. Lot of attempts in increasing the amount of SAP particles in such products and reduction of fluff are made, but as gel blocking has necessitated the use of a fibrous matrix to disperse the SAP particles and separate the SAP particles from one another the reduction of fluff causes a lot of problems.

Therefore many attempts were made to overcome these problems, e.g. fibrous substrates impregnated with superabsorbent polymers are prepared as disclosed in U.S. Pat. No. 5,614,296, U.S. Pat. No. 5,980,996 and 5,756,159 disclose. The fibrous substrates were impregnated with the monomer, which subsequently is polymerized to form an SAP in contact with the fibrous substrate. But the process is very time consuming and the resulting absorbing sheet is very inflexible, which is difficult to handle without breakage.

Furthermore it was tried to produce SAP particles in fiber form. For example U.S. Pat. Nos. 5,147,956 and 4,962,172 disclose such absorbent products and a method of manufacture. Additional patents including U.S. Pat. Nos. 3,867,499, 4,913,869 or 5,667,743 disclose a wet-laid nonwoven fabric comprising a blend of SAP fibers and less absorbing fiber, like woodpulp. WO 98/24832 discloses an absorbent composition containing an acidic and basic material, which can be in fiber form. Furthermore U.S. Pat. No. 6,332,298 discloses multicomponent superabsorbent fibers comprising at least one acidic water absorbing resin and at least one basic water absorbing resin. Such SAP fibers are prepared by extrusion of the rubbery gel of a SAP particles and then dried and optionally surface crosslinked. The fibers obtained are of about at least 10 μm up to 1 mm in diameter and a length of about 1 mm to 10 mm as especially mentioned in U.S. Pat. No. 6,342,298, which discloses a method for producing multicomponent SAP fibers by gel extrusion or dry or wet spinning.

But for use in hygiene articles it is preferred that the fibers have a very high surface area and high fluid absorbency and high fluid retention properties. A very high surface area can be achieved e. g. with fibers in the nano-range, which can be produced with electrospinning.

The preparation of polymer fibers, especially nano- and mesofibers by the electrospinning process, for use in e.g. drug delivery systems, optical and chemosensor materials and filtration is well described in various documents.

According to e. g. D. H. Renecker, H. D. in Nanotech. 7 (1996), page 216 ff. a polymer melt or a polymer solution is typically exposed to a high electrical field at an edge which serves as an electrode. This can be achieved e. g. by extrusion of the polymer melt or polymer solution in an electrical field under low pressure by a cannula connected to one pole of a voltage source. Owing to the resulting electrostatic charge of the polymer melt or polymer solution, there is a material flow directed toward the counterelectrode, which solidifies on the way to the counterelectrode. Depending on the geometry of the electrode nonwovens or assemblies of ordered fibers are obtained by this process.

For use in electrospinning the polymers to be spun have to be solved.

Suitable solutions comprise e.g. organo-soluble polymers such as polyamide, polyacrylnitrile solved in e. g. dimethylformamide or formic acid.

But organic solvents may be undesirable especially in electrospinning of fibres suitable for e.g. hygienic articles or filters used in medical applications as there are often toxic. Therefore water would be a preferred solvent.

Electrospinning of aqueous solutions comprising polyelectrolytes of opposite charge is e. g. disclosed in WO 2008/049397.

US 2010/0013126 deals with electrospinning of aqueous solutions of at least one essentially water-insoluble polymer and at least one water-soluble polymer. The water-soluble polymers form water soluble fibres, which could be easily dissolved by washing with water. In the disclosed method the water-soluble polymers serve as a template for the water-insoluble polymer, and are removed by washing afterwards. Water-soluble polymers such as polyvinyl alcohol, polyvinyl amine, polyethylene oxide, polyvinylpyrrolidone or hydroxypropylcellulose are used. The resulting fibers are water soluble and as mentioned above could be easily dissolved by washing.

In case aqueous solutions of water soluble polymers are spun the resulting fibres or membranes are not water resistant. Therefore to be suitable as absorbents e.g. in medical or hygiene applications such as the use in diapers the fibres need to be stabilized.

One possibility to stabilize such water-soluble fibres is chemical crosslinking by adding cross-linking agent to the aqueous solution before electrospinning. Or as disclosed by Gupta et al in Macromolecules 2004, 37, 9211-9218 the functionalization of water soluble polymers with crosslinkable groups. As described herein water soluble polymers are functionalized with photocurable groups, e.g. cinnamate and then electrospun and simultaneously crosslinked by UV radiation.

The tendency of a crosslinking agent to undergo intermolecular addition reations and problems due to a restricted solubility in the solution to be spun may influence the effectivity of crosslinking and therefore also have an impact on the solubility and absorption properties of the fibres. Furthermore a reduced crosslinking effectivity may also lead to a high extend of residual monomers in the fibre which is also a great disadvantage in case of medical use or e.g. in diapers, leading to skin irritation or other potential health threat.

Generally the amount of crosslinking agent used influences the extent of crosslinking of the polymer. Therefore an adjustment of the extent of crosslinking within the fibres is only possible indirectly by the amount of crosslinking agent used. A change of the extent of crosslinking within the fibres after spinning is not possible.

Therefore it is an object of the present invention to provide water-absorbing fibers (SAP fibers) in the micro- or nanometer scale by spinning, especially electrospinning of water soluble polymers, wherein the crosslinks are directly induced and adjusted within the fiber after spinning.

Furthermore it is an option of the present invention to provide an electrospinning method for producing cross-linked SAP fibers, wherein the amount of crosslinks within the fiber is induced and adjusted after electrospinning.

It is also an object of the present invention to provide hygiene products, fluid-absorbent articles with improved fluid absorption and retention properties.

The object is achieved by a process for producing SAP fibres comprising the steps of electro-spinning a solution, especially an aqueous solution, of at least one water-soluble polymer and subjecting the resulting fibres to UV radiation.

The water soluble polymers are essentially free of any crosslinking agents. This means free of any chemical crosslinker and/or of any modification or functionalization with crosslinkable groups such as thermal sensitive crosslinkable agents. Whereas essentially free means, that if crosslinking agents are present, the amount present has no impact on the CRC of the fibres, therefore preferably the amount of crosslinking agent in the polymer solution should be less than 0.01%, preferably less than 0,005%, more preferably less than 0,003% by weight based on the non-neutralized polymer.

It is preferred that the at least one water-soluble polymer is at least partially neutralized. The degree of neutralization is between 10 to 85 mol %, preferably between 30 to 75 mol %.

The concentration of the water soluble polymer in the aqueous medium is between 5 to 60%, preferably between 8 to 50%, more preferably between 10 to 30% by weight.

During the electrospinning, the fibers are collected by a substrate sheet, such as a nonwoven sheet, e.g. of polypropylene, or an aluminium foil sheet, or substrates of silica treated paper or other suitable material. The substrate is necessary for anti-charging the fibres and to avoid distribution of the fibers throughout the chamber, where the spinning is performed, which will cause disruption of the spinning process.

The resulting fibers which are water soluble are cross-linked by exposing the fibres to UV-light. Wherein the UV radiation has a wavelength of 50 to 350 nm, preferably 100 to 300 nm.

The degree of crosslinking could be determined e.g. by the time and especially the intensity of the UV radiation.

The fibres could be irradiated directly on the substrate sheet such as a nonwoven sheet e.g. of polypropylene or placed on a tray, e.g. a metal sheet or any other suitable sheet. Afterwards the fibers were removed from the substrate.

The resulting water-absorbing polymer fibres preferably have a centrifuge retention capacity (CRC) measured in water of 8 to 30 g/g, preferred at least 5 g/g, more preferred 10 g/g, most preferred at least 20 g/g. The centrifuge retention capacity (CRC) measured in de-ionized water of the water-absorbing polymer fibres is typically less than 60 g/g.

The water soluble polymer suitable for the present invention can be acidic or basic or a mixture of both polymers. Whereas a basic polymer typically containing amino or guanidine groups as in e.g. poly(vinylamine), polyethylenimine or polyvinylguanidine; an acidic polymer prepared by e.g. polymerizing a monomer of the group of ethylenically unsaturated carboxylic acids or anhydrides.

Ethylenically unsaturated carboxylic acid and carboxylic acid anhydride monomers useful in the inventive water-absorbing fibers include acrylic acid, methacrylic acid, ethacrylic acid, α-chloroacrylic acid, α-cyanoacrylic acid, β-methylacrylic acid (crotonic acid), α-phenylacrylic acid, β-acryloxy-propionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, and maleic anhydride. Particularly preferred monomers are acrylic acid and methacrylic acid. Very particular preference is given to acrylic acid.

Further suitable monomers are, for example, ethylenically unsaturated sulfonic acids. Ethylenically unsaturated sulfonic acid monomers include aliphatic or aromatic vinyl sulfonic acids, such as vinylsulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, sulfopropyl methacrylate, 2-hydroxy-3methacryloxypropyl sulfonic acid, and 2-acrylamide-2methylpropane sulfonic acid (AMPS).

Polymerization of such monomers, or mixtures thereof, if present, most commonly is performed by free radical processes. The resulting polymers such as polyacrylic acid, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly (vinylphosphoric acid), poly(vinylsulfuric acid), sulfonated polystyrene, poly(aspartic acid), poly(lactic acid), and mixtures thereof, whereas polyacrylic acid for electrospinning are solved, preferably in water.

Preferably the acidic water soluble polymer is polyacrylic acid and the basic polymer is polyvinylamine.

The polymer solutions are typically partially neutralized. Neutralization is preferably carried out at the monomer stage. This is typically done by mixing with the neutralizing agent as an aqueous solution or preferably also as a solid. The degree of neutralization is preferably from 10 to 85 mol %, for acidic polymer gels more preferably from 30 to 60 mol %, most preferably from 35 to 55 mol %, and for neutral polymer gels more preferably from 65 to 80 mol %, most preferably from 70 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts, such as the salt of triethanolamine. Particularly preferred alkali metals are sodium and potassium, but very particular preference is given to sodium hydroxide, sodium carbonate or sodium hydrogencarbonate and also mixtures thereof.

The solutions suitable for electrospinning according to the present invention are essentially free of crosslinking agents to crosslink the resulting SAP-fibers to a sufficient extent such that the polymer fibers are water insoluble and suited for the intended applications.

According to the invention the crosslinking is performed by UV radiation of the electrospun fibres, which are essentially free of crosslinking agents.

For the electro-spinning process it is important that the polymer concentration in the aqueous medium is between 5% and 60%, preferably between 8% and 50%, more preferably between 10 to 30% by weight.

When exclusively water is used as the solvent, a surfactant may be advantageously added. This improve the electrospinning process and the fiber properties. Suitable surfactants are surfactants comprising e.g. (oligo)oxyalkene groups, or carbohydrate groups or amine oxides.

The polymer solution according to the invention can be electrospun using any methods known to those skilled in the art.

The distance between the cannula and the counterelectrode functioning as the collector, and the voltage between the electrodes, is preferably adjusted in such a way that an electrical field of 1 to 6 kV/cm, preferably from 1.5 to 5 kV/cm, more preferably from 2 to 4.5 kV/cm and most preferably from 2.5 to 4 kV/cm is formed between the electrodes. Good results are achieved especially when the internal diameter of the cannula is from 50 to 500 μm.

A suitable electrospinning apparatus comprises a syringe which is provided at its tip with a capillary die connected to one pole of a voltage source and is for accommodating the inventive solution. Good results are achieved when the internal diameter of the capillary die is from 50 to 500 μm. Opposite the exit of the capillary die, at a distance of about 20 cm, preferably of about 16 cm, more preferably of about 14 cm, most preferably of about 13 cm, a counterelectrode is arranged, e.g. a square counterelectrode, or collecting electrode connected to the other pole of the voltage source, which functions as the collector for the fibers formed. During the operation of the apparatus, a voltage between 0 kV and 82 kV is set at the electrodes in such a way that an electrical field of preferably from 1 to 6 kV/cm, more preferably from 1.5 to 5 kV/cm, preferentially from 2 to 4.5 kV/cm and most preferably from 2.5 to 4 kV/cm forms between the electrodes. Owing to the electrostatic charge a material flow directed toward the counterelectrode forms, which solidifies on the way to the counterelectrode with fiber formation, as a consequence of which fibers with diameters in the micro- and nanometer range are deposited on the counterelectrode. Generally a temperature range for spinning is chosen of 10 to 30° C., preferably 15 to 25° C., more preferably 21 to 27° C. and a humidity range of 10 to 45% RH, preferably 20 to 35% RH.

With the aforementioned apparatus, in accordance with the invention, a solution of at least one essentially water-soluble polymer in an aqueous medium is electrospun.

During the electrospinning, the fibers are collected by a substrate sheet, such as a nonwoven sheet, e.g. of polypropylene, or an aluminium foil sheet, or substrates of silica treated paper or other suitable material. The substrate is necessary for anti-charging the fibres and to avoid distribution of the fibers throughout the chamber, where the spinning is performed, which will cause disruption of the spinning process.

After electro-spinning, the polymer fibers are subjected to UV radiation to induce the crosslinks within the fibres. In general, crosslinking renders the fibers substantially water insoluble, and, in part, serves to determine the absorption capacity of the fibers. Thus the e.g. absorption/swelling and/or mechanical properties of the water-absorbing fibres may be adapted to their intended use.

To induce the crosslinking of the fibres the nonwoven substrate of the e-spinning apparatus or any other substrate suitable, with the E-spun fibres on top are exposed to UV radiation The irradiation is effected by customary processes known to those skilled in the art. UV radiation is understood to mean radiation of wavelengths from 50 to 350 nm, preferably from 100 to 300 nm. For fibres of polyacrylic polymer, a wavelength of 254 nm is preferred.

Suitable for irradiation are conventional UV radiators are typically used, such as for example, high-pressure, medium-pressure and low pressure mercury radiators, and also fluorescent tubes, pulse radiators, lasers, metal halide radiators, xenon radiators and halogen radiators or excimer radiators. The radiation dose typically sufficient for crosslinking is within the range from 10 to 5000 mJ/cm$^2$.

Generally the intensity of the light and irradiation time suitable are dependent on the polymer of the fibres. Usually the intensity of the UV radiation used is between 15 to 44 mWcm$^{-2}$, preferably 20 to 30 mWcm$^{-2}$.

The intensity may be varied by the distance between the UV source and the fibres. A distance of 1 to 10 cm is preferred, more preferred a distance of 2 to 5 cm are chosen. The fibres are radiated for a time period of preferably 0.1 seconds to 60 minutes, more preferably of 0.5 seconds to 30 minutes, especially of 1 second to 15 minutes. The radiation time varies in dependence of the polymers to be radiated and the degree of neutralization. Usually an increase in the degree of neutralization and an increase in the time of exposure will rise the amount of crosslinks within the fibres. The irradiation of the fibres can be carried out at room temperature with satisfactory results.

The fibres can be irradiated in a gas or gas mixture. Preferred gases or gas mixtures are air, water vapor and/or inert gas, such as nitrogen, carbon dioxide, noble gases and also mixtures thereof. Very particular preference is given to performing the irradiation of the fibres in an atmosphere composed of air.

To prevent oxidation reactions during UV exposure, which may have a negative impact on the properties of the water-absorbing fibres inert gas such as nitrogen is preferred.

In the embodiment in which the fibres are irradiated in a gas/gas mixture, the pressure in the gas space is adjusted to a value in the range from 0.001 to 10 bar, 10 preferably from 0.1 to 3 bar, more preferably from 0.5 to 1.5 bar and most preferably to standard pressure.

The CRC of the fibres can be adjusted by this procedure as the CRC is dependent on the swelling properties of the water-absorbing fibres. The resulting water-absorbing polymer fibres preferably have a centrifuge retention capacity (CRC) measured in water of 8 to 30 g/g, preferred at least 5 g/g, more preferred 10 g/g, most preferred at least 20 g/g. The centrifuge retention capacity (CRC) measured in water of the water-absorbing polymer fibres is typically less than 60 g/g. The centrifuge retention capacity (CRC) is determined by EDANA recommended test method No. WSP 241.2-5 "Centrifuge Retention Capacity" except for the measurements in water, where de-ionized water is used instead of saline.

To determine the best suited crosslinking conditions for an intended use of the fibres e.g. a preferred time range for the exposure to UV light of a given fibre or a preferred degree of neutralization resulting in the desired CRC value or range, the dissolving test as disclosed herein is very useful.

For testing, the water-absorbing fibres are exposed to a definite amount of de-ionized water. In case the fibres are not crosslinked, they dissolve totally, in case they are at least partly cross-linked a soft-diluted gel is formed and in case they are totally crosslinked a gel is formed. Fibres which are not or only partly crosslinked are easily detected by this method.

Then the CRC can be measured for the crosslinked fibres. The resulting CRC should preferably be in the range of 8 to 30 g/g, measured in de-ionized water. To adapt the CRC of the fibres to a special application or use, the conditions, e.g. intensity, time of exposure to UV light and/or the degree of neutralisation of the polymer solution could be varied.

An increase of exposure time raise the number of cross-links. Furthermore an increase of neutralisation of the polymer solution may especially in combination with an increase in intensity or exposure time of the UV radiation raise the number of crosslinks in the electrospun fibres. Therefore the amount of crosslinking and so the absorption feature of the fibres may be adjusted easily for an intended use.

After UV-radiation, the moisture content in fibers is preferably 0.5 to 15% by weight, more preferably 1 to 10% by weight, most preferably 3 to 5% by weight, the residual moisture content being determined by EDANA recommended test method No. WSP 230.2-5 "Moisture Content".

In the case of a too high residual moisture content, the dried polymer fibers have a too low glass transition temperature $T_g$ and can be processed further only with difficulty. In the case of a too low residual moisture content, the dried polymer gel is too brittle and, in the subsequent comminution steps, undesirably large amounts of polymer fibers with an excessively low fiber length are obtained.

The fibers combine a high water resistance with a good mechanical stability. Furthermore the SAP fibers according to the present invention absorb liquids quickly, provide a good fluid permeability and conductivity into and through the SAP fiber and have high gel strength such that the hydrogel formed from the SAP fibers does not deform or flow under an applied pressure or stress.

The diameter of the inventive fibers is preferably less than 3 µm, preferably less than 2 µm, more preferably less than 1 µm, particularly less than 500 nm, very particularly less than 300 nm. The length of the fibers depends upon the intended use and is generally from 50 µm up to several kilometres.

Preferred are crosslinked water-absorbing polymer fibres with a centrifuge retention capacity (CRC) of at least 5 g/g in water, a fiber diameter of 0.3 to 2 µm, a degree of neutralization of 10 to 80 mol %, which are essentially free of crosslinking agent.

Whereas essentially free means as described above, that if crosslinking agents are present, the amount present has no impact on the CRC of the fibres.

To further improve the properties of the electrospun fibres, the polymer fibers can be surface-coated and/or remoisturized.

Suitable surface-coatings for controlling the acquisition behavior and improving the permeability (SFC or GBP) are, for example, inorganic inert substances, such as water-insoluble metal salts, organic polymers, cationic polymers and polyvalent metal cations. Suitable coatings for improving the color stability are, for example reducing agents and anti-oxidants. Suitable coatings for dust binding are, for example, polyols.

Suitable inorganic inert substances are silicates such as montmorillonite, kaolinite and talc, zeolites, activated carbons, polysilicic acids, magnesium carbonate, calcium carbonate, calcium phosphate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the fluid-absorbent polymer fibers are surface-coated with inorganic inert substances, the amount of inorganic inert substances used, based on the fluid-absorbent polymer fibers, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene, polypropylene, polyamides or polytetrafluoro-ethylene. Other examples are styrene-isoprene-styrene block-copoly-mers or styrene-butadiene-styrene block-copolymers.

Suitable cationic polymers are polyalkylenepolyamines, cationic derivatives of polyacrylamides, polyethyleneimines and polyquaternary amines.

Polyquaternary amines are, for example, condensation products of hexamethylenedi-amine, dimethylamine and epichlorohydrin, condensation products of dimethylamine and epichlorohydrin, copolymers of hydroxyethylcellulose and diallyldimethylammo-nium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the fiber surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, polyfunctional acids or poly-functional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine or a partially hydrolyzed polyvinylformamide.

The cationic polymers may be used as a solution in an aqueous or water-miscible solvent, as dispersion in an aqueous or water-miscible dispersant or in substance.

When the fluid-absorbent polymer fibers are coated with a cationic polymer, the use amount of cationic polymer based on the fluid-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable polyvalent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^{+}$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, hydroxide, carbonate, nitrate and sulfate. The metal salts are preferably used as a solution or as a stable aqueous colloidal dispersion. The solvents used for the metal salts may be water, alcohols, dimethylfor-mamide, dimethyl sulfoxide and mixtures thereof. Particular preference is given to water and water/alcohol mixtures, such as water/methanol, water/isopropanol, water/1,3-propanediole, water/1,2-propandiole/1,4-butanediole or water/propylene glycol.

When the fluid-absorbent polymer fibers are coated with a polyvalent metal cation, the amount of polyvalent metal cation used, based on the fluid-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophos-phite, salts of sulfinic acids, for example the disodium salt of 2-hydroxy-2-sulfinato-acetic acid, and addition products of aldehydes, for example the disodium salt of 2-hy-droxy-2-sulfonatoacetic acid. The reducing agent used can be, however, a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

The reducing agents are typically used in the form of a solution in a suitable solvent, preferably water. The reducing agent may be used as a pure substance or any mixture of the above reducing agents may be used.

When the fluid-absorbent polymer fibers are coated with a reducing agent, the amount of reducing agent used, based on the fluid-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpropane, glycerol, sorbitol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the fluid-absorbent polymer fibers only insignificantly. The polyols are preferably used as a solution in aqueous or water-miscible solvents.

When the fluid-absorbent polymer fibers are coated with a polyol, the use amount of polyol, based on the fluid-absorbent polymer particles, is preferably from 0.005 to 2% by weight, more preferably from 0.01 to 1% by weight, most preferably from 0.05 to 0.5% by weight.

The surface-coating is preferably performed by spaying the respective solutions on the fibers. The present invention is also related to fluid absorbent articles comprising SAP-fibres according to the invention. Fluid absorbent articles are understood to mean, for example, incontinence pads and incontinence pants for adults, or diapers for babies.

Furthermore the invention is directed to a fluid absorbent article comprising a layer containing water-absorbing fibres (SAP fibres), whereas the layer could comprise fluid-absorbent polymer fibers according to the present invention or mixtures of the inventive fibres and other fibres. The layer preferably contains SAP fibers in an amount of about 0.1% to 100% by total weight of fibres.

For example, the resulting fluid absorbent article may have the following construction:
(A) an upper liquid-pervious topsheet
(B) a lower liquid-impervious layer
(C) a layer of water-absorbing fibres or mixtures of water-absorbing fibres with fluff, between topsheet (A) and layer (B),
(D) optionally a tissue layer immediately above and below the layer of water-absorbing fibres (C) and
(E) optionally an absorption and distribution layer between topsheet (A) and the layer of water-absorbing fibres (C).

The thickness of the layer of water-absorbing fibres or mixtures of water-absorbing fibres with fluff can be varied. For example, the water-absorbing layer (C) may have less material, for example, in the outer region. Cutouts and channels are likewise possible.

Examples of fibers to be mixed with the inventive SAP fibres include cellulose fibers such as fluff pulp and cellulose of the cotton type. The materials (soft- or hardwoods), production processes such as chemical pulp, semichemical pulp, chemothermomechanical pulp (CTMP) and bleaching processes are not particularly restricted. For example, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The fiber cross section may be round or angular, or else have another shape, for example like that of a butterfly.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. In addition, the addition of thermoplastic fibers means that there is an increase in the present pore dimensions after the heat treatment has taken place. This makes it possible, by continuous metered addition of thermoplastic fibers during the formation of the absorbent layer, to continuously increase the fraction of thermoplastic fibers in the direction of the topsheet, which results in a similarly continuous increase in the pore sizes. Thermoplastic fibers can be formed from a multitude of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9000 meters) in diameter may preferably be used. Preferred thermoplastic fibers are from 3 to 50 mm in length, particularly preferred thermoplastic fibers are from 6 to 12 mm in length. The preferred diameter for the thermoplastic fibers is in the range from 1.4 to 10 decitex, and the range from 1.7 to 3.3 decitex (gram per 10 000 meters) is particularly preferred. The form of the fibers may vary; examples include woven types, narrow cylindrical types, cut/split yarn types, staple fiber types and continuous filament fiber types.

Suitable hydrophilic fibers include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilizing hydrophobic fibers, for example the treatment of thermoplastic fibers obtained from polyolefins (e.g. polyethylene or polypropylene, polyamides, polystyrenes, polyurethanes, etc.) with surfactants or silica. However, for reasons of cost and availability, cellulose fibers are preferred.

The liquid-impervious topsheet (A) is a layer in direct contact with the skin. The material for this purpose consists of customary synthetic or semisynthetic fibers or films of polyester, polyolefins, rayon or natural fibers such as cotton. In the case of nonwoven materials, the fibers should generally be bound by binders such as polyacrylates. Preferred materials are polyester, rayon and blends thereof, polyethylene and polypropylene. Examples of liquid-pervious layers are described in WO 99/57355 A1, EP 1 023 883 A2.

The liquid-impervious layer (B) generally consists of a film of polyethylene or polypropylene. A nonwoven may be laminated onto the layer (B) for better tactile properties on the outside.

Absorption and distribution layers (E) are typically produced from nonwovens which have very good wicking action, in order to absorb and to distribute the liquid rapidly. They also improve rewetting. When pressure on the diaper causes the water-absorbing composite to release liquid, the absorption and distribution layer (E) prevents this liquid from coming into contact with the skin of the user.

Suitable nonwovens are thermally bonded or resin-bonded fibers based on polypropylene and/or polyester fibers with a basis weight of 25 to 70 gms, for example Curadis@, Curadis® EPS, Curadis® ATP and Curadis® RB (Albis SPA, IT).

Further suitable absorption and distribution layers (E) are obtained by "airthroughbonding" and are obtainable under the Acquitex® (Texus SPA, IT) and Dry Web® (Libeltex BVBA, NL) trademarks.

Methods

Solid Content

The solids content within the solution is determined gravimetrically by means of a Mettler Toledo HR73 halogen moisture analyzer, by heating approx. 1 ml of the sample to 200° C. within 2 minutes and drying the sample to constant weight and then weighing it.

Size of the Fibers

The size, i.e. the diameter and the length of the fibers, is determined by evaluating electron micrographs (using a Scanning Electronic Microscope (SEM) to determine the fiber diameters).

Centrifuge Retention Capacity (CRC)

The centrifuge retention capacity of the fluid-absorbent polymer particles is determined by the EDANA recommended test method No. WSP 241.2-5 "Centrifuge Retention Capacity", wherein for higher values of the centrifuge retention capacity larger tea bags have to be used due to bursting of the tea-bag upon hydration. The CRC measurements are performed in 0.9 wt % of NaCl saline or de-ionized water.

Moisture Content

The moisture content of the fluid-absorbent polymer particles is determined by the EDANA recommended test method No. WSP 230.2-5 "Moisture Content".

Residual Monomers

The level of residual monomers in the fluid-absorbent polymer particles is determined by the EDANA recommended test method No. WSP 210.2-5 "Residual Monomers".

The EDANA test methods are obtainable, for example, from the EDANA, Avenue Eugene Plasky 157, B-1030 Brussels, Belgium.

Dissolving Test

The degree of internal crosslinking of the fibres are qualitatively measured by a dissolving test:
1. 0.02 gram of fiber film sample are put it into a disk or on a glass slide.
2. About 0.4 gram (water weight/sample weight ~20:1) of de-ionized water are dropped with a pipe drop to the fiber film sample.
3. The resulting dissolving situation of the tested sample:
   A the sample dissolved in water totally, no gel formed: Indication that there are no internal-cross linkers formed;
   B the fiber film absorbed water and a stable gel is formed: Indication that throughout the fibres internally-cross-linkers formed;
   C the test sample partially dissolved, and a soft diluted gel is formed: Indication that the fiber films were partially internally-crosslinked.

EXAMPLES

The following examples illustrate the preparation of the SAP-fibers of the present invention.

For the examples a commercial available poly-acrylic acid (PAA) named Sokalan® PA 110S (about 35% of polymer, available from, BASF SE, Carl-Bosch-Strasse 38, 6703, Ludwigshafen, Germany) is diluted to a suitable concentration with de-ionized water, and the resulting solution is neutralized to designed degree levels. Further a selected crosslinking agent is dissolved into the solution. This preparation should unless stated otherwise, be carried out at an ambient temperature of 23±2° C. and an atmospheric humidity of 50±10%.

Electrospinning

The electrospinning was performed with an electrospinning spider NS LAB 200, commercial available from Elmarco s.r.o. V Horkach 76/18, 460 07, Liberec 9, Czech Republic.

For each solution (Examples 1 to 20) about 20 grams are poured into the Nanospider®.s low volume 20 ml spinning tube with small cylinder spinning electrode. The Tube is then placed into Nanospider® chamber with Elmarco's (anti-stable charge treated) nonwoven substrate. The cylinder in the tube is positioned 13-14 cm in a distance from the collecting electrode. Generally a temperature range for spinning is chosen to 10 to 30° C. range and humidity range of 10 to 45% RH. For the polymer used in Examples 1 to 12 the optimum conditions are a temperature range of 21 to 27° C. and humidity in the range of 20-35% RH.

Providing an electric field strength in the range of 1 to 5 kv/cm the E-spun fibers are made and collected on the selected substrates.

UV Radiation Process

The nonwoven substrate with the E-spun fibres on top was cut into squares of about 6 inches×6 inch size. These E-spun fiber samples were put into a sample tray and exposed to UV radiation (UV set used is a UVO cleaner, with the peak power wavelength of 254 nm, available from Jelight Company Inc., Model No 42-220, 2 Mason, Irvin, Calif. 92618, USA). For the examples a distance of about 3 cm of the UV-lamp to the sample are chosen. The exposure time varied in dependence of the polymers used and the degree of neutralization. During radiation the sample could be exposed to nitrogen gas for protection. The resulting cross-linked E-spun fiber samples were taken out from the sample tray.

For each of the resulting fibres the CRC and the dissolving in de-ionized water was measured according to the above mentioned methods. The results and the times of UV radiation are summarized in table 1.

Example 1

Comparative

A 20% PAA solution is prepared made by mixing 228.57 grams of 35% PAA (poly-acrylic acid) solution (Sokalan® PA 110S, BASF SE, Carl-Bosch-Strasse 38, 6703, Ludwigshafen, Germany) with 171.43 grams of de-ionic water by using of a stir plate with a stir bar for 30 minutes. Then doing e-spinning. The resulting fibres are not exposed to UV-radiation.

Example 2

Comparative

The same as example 1, but after E-spinning, the E-spun fibers are exposed for 3 min to UV radiation to induce self-crosslinking.

Example 3

Comparative 50 grams of the solution of Example 1 are mixed with 3.33 grams of Sodium Hydroxide Solution Certified 50/w/w (50/50 sodium hydroxide/water weight ratio, available from Fisher Scientific, 3970 Johns Creek Ct., Suit 500, Suwanee, Ga. 30024, USA) and stirred for 60 minutes on stir plate with a stir bar. Small air bubbles are seen throughout the solution, so the solution is sit until all of the air bubbles are dissipated. The degree of neutralization (DN) of the PAA solution is 15%. The E-spun fibers are exposed 3 min to the UV radiation.

Example 4

Inventive

The same as example 3, except the E-spun fibers are exposed 5 min to the UV radiation.

Example 5

Comparative 50 grams of the solution of Example 1 are mixed with 6.67 grams of Sodium Hydroxide Solution Certified 50/w/w (50/50 sodium hydroxide/water weight ratio, available from Fisher Scientific, 3970 Johns Creek Ct., Suit 500, Suwanee, Ga. 30024, USA) and stirred for 60 minutes on stir plate with a stir bar. Small air bubbles are seen throughout the solution, so the solution is sit until all of the air bubbles are dissipated. The degree of neutralization (DN) of the PAA solution is 30%. The E-spun fibers are exposed 5 min to the UV radiation.

Example 6

Inventive

The same as example 5, except the E-spun fibers are exposed 15 min to the UV radiation.

Example 7

Inventive 50 grams of the solution of Example 1 are mixed with 11.11 grams of Sodium Hydroxide Solution Certified 50/w/w (50/50 sodium hydroxide/water weight ratio, available from Fisher Scientific, 3970 Johns Creek Ct., Suit 500, Suwanee, Ga. 30024, USA) and stirred for 60 minutes on stir plate with a stir bar. Small air bubbles are seen throughout the solution, so the solution is sit until all of the air bubbles are dissipated. The degree of neutralization (DN) of the PAA solution is 50%. The E-spun fibers are exposed 20 min to the UV radiation.

Example 8

Comparative

Denacol EX-810 (Nagase ChemteX Corporation Tasuno City Hyogo, Japan) is used as a cross-linker; 0.05 grams of Denacol EX-810 are added into 50 grams of the solution of Example 1 and stirred about 30 minutes with a stir bar. The E-spun fibres are not exposed to UV radiation. The E-spun fibers are put into a 130° C. oven for 60 minutes.

Example 9

Comparative 0.03 grams of Heonon/PDO mixture (as a crosslinker) are added to 50 grams of a DN 50% PAA solution according to example 7, and stirred about 30 minutes with a stir bar. The E-spun fibres are not exposed to UV radiation. The E-spun fibers are put into a 180° C. oven for 60 minutes.

Example 10

Comparative

Denacol EX-810 (Nagase ChemteX Corporation Tasuno City Hyogo, Japan) is used as a cross-linker; 0.05 grams of Denacol EX-810 are added into 50 grams of a DN 50% PAA solution according to example 7 and stirred about 30 minutes with a stir bar. The E-spun fibres are not exposed to UV radiation. The E-spun fibers are put into a 130° C. oven for 60 minutes.

Example 11

Inventive 70 gram of a 4 wt% salt free Polyvinylamine (PVAm, GK 2873/035, average molecular weight is about 340,000) and 30 gram of a 4 wt % salt free Polyvinylamine (GK 2214/131, average molecular weight is about 45,000) are mixed; 0.01 gram of triton X-100 (available from Sigma-Aldrich) added and stirred about 30 minutes with a stir bar. The E-spun fibers are exposed for 3 min to UV radiation.

Preparation of Polyvinylamine

All given percentages are weight % if not mentioned otherwise.

Solid contents were measured in a forced draft oven: 2 h at 140° C.

K-values are determined according to H. Fikentscher, Cellulosechemie, volume 13 pages 48-64 and 71-74 (1932). The specific conditions are mentioned in brackets Molecular Weight is determined via static light scattering in an aqueous 0.6% NaCl solution at a pH of 7.6

The degree of hydrolysis is determined by measuring the formed formate. For this purpose an enzymatic test set for formic acid of R-Biopharm AG, Darmstadt, Germany is used Preparation of Polyvinylamine GK 2214/131

A 3 necked 4 litre glass vessel equipped with anchor stirrer, condenser, thermo couple and nitrogen inlet is charged with 1931.4 g of distilled water and 7.7 g of 75% phosphoric acid. While stirring at 100 rpm 10.1 g of 25% caustic soda is added to achieve a pH of 6.5. While bubbling nitrogen through the solution for 30 min the vessel is heated to 78° C. Vacuum is applied to such a level (about 480 mbar) that the buffer solution starts boiling without distilling off a significant amount. 759.1 g of N-vinylformamide and a solution of 13.5 g of 2,2"-Azobis(2-methylpropionamide)-dihydrochloride in 135 g of distilled water is added in 3 hours simultaneously. After about 20 min from the start of the two feeds polymerisation become visible by an increased distillation rate. During the polymerization water is distilled off to remove the polymerization heat. During the 3 hours temperature is kept constant at 78° C. by adjusting the vacuum accordingly. After the end of the 2 feeds the internal temperature is kept at 78° C. for another 2 h. During the whole polymerisation process 783 g of water are distilled off. Vacuum is released by venting with nitrogen and a sample is taken to determine the analytical data. A viscous lightly yellow solution of Polyvinylformamide (PVFA) is obtained.

K-value (1% in water): 49
Mw 48 000
Solid content: 36,6%

The achieved polymer solution is heated to 80° C. To hydrolyse the PVFA 55.1 g of a 40% aqueous solution of sodium-hydrogensulphite and 1863.7 g of 25% aqueous caustic soda is added. The reaction mixture is held for 6 h at 80° C. After cooling to room temperature an aqueous solution of polyvinylamine (PVAm) with a degree of hydrolysis of 98 mol % is obtained.

3937 g of the PVAm solution is diluted with 2384 g distilled water and heated to 50° C. To remove the formate formed during hydrolysis the solution is ultra-filtrated using a MPS-34 membrane of Kiryat Weizmann LTD, Rehovot, Israel with a cut of limit of 500 Dalton. In total 26545 g of filtrate are replaced by distilled water. By this means >99.5% of the formate is removed. The final product has a solid content 8.6%

Preparation of Polyvinylamine GK 2873/035

A 3 necked 4 litre glass vessel equipped with anchor stirrer, condenser, thermo couple and nitrogen inlet is charged with 1235.3 g of distilled water and 2.9 g of 75% phosphoric acid. While stirring at 100 rpm 4.3 g of 25% caustic soda is added to achieve a pH of 6.5. While bubbling nitrogen through the solution for 30 min the vessel is heated to 77° C. Vacuum is applied to such a level (about 410 mbar) that the buffer solution starts boiling without distilling off a significant amount. Simultaneously a feed of 262.3 g of N-vinylformamide (VFA) and a feed of 1.2 g of 2,2'-Azobis (2-methylpropionamide)-dihydrochloride in 65.0 g of distilled water is started. The VFA feed lasts 2 h while the initiator feed is added in 2 h 50 min. After about 20 min from the start of the two feeds polymerization becomes visible by an increased distillation rate. During the polymerisation water is distilled off to remove the polymerization heat. During the feeding period temperature is kept constant at 77° C. by adjusting the vacuum accordingly. After the end of the initiator feed the internal temperature is kept at 77° C. for another 3 h. During the whole polymerisation process 260 g of water was distilled off. Vacuum is released by venting with nitrogen and 708.5 g distilled water is added. A sample is taken to determine the analytical data. A viscous lightly yellow solution of polyvinylformamide (PVFA) is obtained.

K-value (1% in water): 89
Mw 340 000
Solid content: 13.0%

The achieved polymer solution is heated to 80° C. To hydrolyse the PVFA 7.1 g of a 40% aqueous solution of sodium-hydrogensulphite and 1096.1g of 25% aqueous caustic soda is added. The reaction mixture is held for 7 h at 80° C. After cooling to room temperature an aqueous solution of polyvinylamine with a degree of hydrolysis of 99 mol % is obtained.

2958 g of the PVAm solution is diluted with 3106 g distilled water and heated to 50° C. To remove the formate formed during hydrolysis the solution is ultra-filtrated at 50° C. using a membrane of A/G Technology Corporation, Needham, Mass., USA, Israel with a cut of limit of 3000 Dalton. In total 27072 g of filtrate is replaced by distilled water. By this means >99.8% of the formate was removed. The final product has a solid content of 6.5%

Example 12

Inventive

The same as example 11, except the E-spun fibers are exposed for 5 min to the UV radiation.

Example 13

Comparative 50 grams of example 11 are mixed with 0.03 grams of hydroxypropyl acrylate (HPA, made by BASF SE in Germany, available from BASF Corporation, 2090 Wagner Street, Vandalia, Ill. 62471, USA), and stirred about 30 minutes with a stir bar. The E-spun fibers are not exposed to UV radiation. The E-spun fibers are put into the oven with 80° C. for 60 minutes to activate the crosslinking agent.

TABLE 1

Results of the measurements

| Example | PAA concentration % | Degree of neutralization % | Crosslinker % | dissolving in water | UV exposure time Min | E-spun fiber diameter (μm) | CRC in water (g/g) | CRC (g/g) |
|---|---|---|---|---|---|---|---|---|
| 1 (comparative) | 20 | 0 | | Yes | 0 | 0.3 to 3.0 | 0 | 0 |
| 2 (comparative) | 20 | 0 | | No | 3 | 0.3 to 3.0 | 4.5 | 0.8 |
| 3 (comparative) | 20 | 15 | | Partially | 3 | 0.5 to 3.0 | N/A | N/A |
| 4 (inventive) | 20 | 15 | | No | 5 | 0.5 to 3.0 | 9.5 | 1.5 |
| 5 (comparative) | 20 | 30 | | Partially | 5 | 0.5 to 3.0 | N/A | N/A |
| 6 (inventive) | 20 | 30 | | No | 15 | 0.5 to 3.0 | 20.8 | 8.2 |
| 7 (inventive) | 20 | 50 | | No | 20 | 0.5 to 3.0 | 21 | 8.2 |
| 8 (comparative) | 20 | 0 | 0.5 | No | 0 | 0.3 to 2.0 | 7.6 | 5.4 |
| 9 (comparative) | 20 | 50 | 0.3 | No | 0 | 0.3 to 3.0 | 28.4 | 17.3 |
| 10 (comparative) | 20 | 50 | 0.5 | No | 0 | 0.4 to 2.0 | N/A | 23 |
| 11 (inventive) | 7.5 | 0 | | No | 3 | 0.3 to 2.0 | 20.8 | 15 |
| 12 (inventive) | 7.5 | 0 | | No | 5 | 0.3 to 2.0 | 14.2 | 12.4 |
| 13 (comparative) | 7.5 | 0 | 1.0 | No | 0 | 0.3 to 2.0 | 9.4 | 6.7 |

The invention claimed is:

1. A process for producing water-absorbing polymer fibres comprising:
   a) spinning a solution of at least one water-soluble polymer, and
   b) subjecting the resulting fibres to UV radiation,
   wherein the water soluble polymer solution is free of crosslinking agent.

2. The process according to claim 1, wherein the spinning process is electrospinning.

3. The process according to claim 1, wherein the water soluble polymer is at least partially neutralized.

4. The process according to claim 3, wherein a degree of neutralization is between 10 and 85 mol %.

5. The process according to claim 1, wherein the polymer concentration in an aqueous medium is between 5% to 60% by weight.

6. The process according to claim 1, wherein the UV radiation has a wavelength of 50 to 350 nm.

7. The process according to claim 1, wherein the fibres have a centrifuge retention capacity (CRC) of at least 5 g/g in de-ionized water.

8. The process according to claim 1, wherein the water soluble polymer is anionic or cationic or a mixture of both.

9. The process according to claim 1, wherein the water soluble polymer is polyacrylic acid and/or polyvinylamine.

10. Water-absorbing polymer fibres obtained by a process according to claim 1.

11. The fibres according to claim 10 having a diameter not greater than 3 μm.

12. The fibres according to claim 10 having a centrifuge retention capacity (CRC) in de-ionized water of at least 5 g/g.

13. Water-absorbing polymer fibres having a centrifuge retention capacity (CRC) of at least 5 g/g, a fiber diameter of 0.3 to 2 μm, a degree of neutralization of 10 to 80 mol %, and free of crosslinking agent.

14. A fluid absorbent article comprising fibres according to claim 10.

15. The fluid absorbent article according to claim 14, comprising a core containing about 0.1% to 100% by weight of the fibres.

16. A fluid absorbent article comprising fibres according to claim 13.

17. The fluid absorbent article according to claim 16, comprising a core containing about 0.1% to 100% by weight of the fibres.

* * * * *